United States Patent [19]

Dohara et al.

[11] Patent Number: 5,064,639

[45] **Date of Patent: * Nov. 12, 1991**

[54] INSECTICIDAL AEROSOL

[75] Inventors: Kazunobu Dohara, Sakai; Tadahiro Matsunaga, Kobe; Motomitsu Shiraishi, Amagasaki; Goro Shinjo, Toyonaka, all of Japan

[73] Assignee: Sumitomo Chemical Company, Limited, Osaka, Japan

[ * ] Notice: The portion of the term of this patent subsequent to Oct. 8, 2008 has been disclaimed.

[21] Appl. No.: 281,519

[22] Filed: Dec. 8, 1988

[30] Foreign Application Priority Data

Dec. 15, 1987 [JP] Japan ................................ 62-318184

[51] Int. Cl.5 ................................................ A61L 9/04

[52] U.S. Cl. ........................................ 424/45; 424/43; 424/405; 424/408; 424/409

[58] Field of Search ................... 424/43, 45, 405, 409, 424/408

[56] References Cited

U.S. PATENT DOCUMENTS

| | | | |
|---|---|---|---|
| 4,450,253 | 5/1984 | Suk | 524/378 |
| 4,518,734 | 5/1985 | Brouilette et al. | 524/378 |
| 4,604,226 | 8/1986 | Bartlett | 252/389 |

FOREIGN PATENT DOCUMENTS

| | | |
|---|---|---|
| 0006212 | 9/1980 | European Pat. Off. . |
| 0032779 | 7/1981 | European Pat. Off. . |
| 069906A | 1/1983 | European Pat. Off. . |
| 54-095737 | 7/1979 | Japan . |
| 60-104003 | 6/1985 | Japan . |
| 60-104004 | 6/1985 | Japan . |
| 61-45601 | 10/1986 | Japan . |

*Primary Examiner*—Lester L. Lee
*Assistant Examiner*—E. J. Kraus
*Attorney, Agent, or Firm*—Stevens, Davis, Miller & Mosher

[57] ABSTRACT

A mono-layer liquid phase type water-based insecticidal aerosol comprises a base liquid for aerosol containing at least one specific pyrethroidal compound, a specific organic solvent and a specific buffer solution, which base liquid has a pH of from 7.0 to 11.0, and dimethyl ether as a propellant. The aerosol according to the present invention has a long-term storage stability as well as an excellent insecticidal activity and causes no degradation of the container.

5 Claims, No Drawings

INSECTICIDAL AEROSOL

The present invention relates to a mono-layer liquid phase type water-based insecticidal aerosol.

Recently, since water-based insecticidal aerosols can be averted from inflammability and toxicity to mammals, and since their manufacturing cost is relatively low, various developments have been forwarded on them.

However, most of the conventionally known water-based aerosols are the so-called two-layer liquid phase type water-based ones, that is, the liquid phase separates in two layers. Consequently, before the use of such aerosols, homogenizing the liquid phase by shaking is not avoidable.

To avoid the inconvenience, the so-called mono-layer liquid phase type water-based insecticidal aerosols have been developped. This type of aerosols can be prepared by dispersing an insecticidally active ingredient such as a pyrethroidal insecticidal compound in water with the aid of ethanol, etc. followed by blending thereto a propellant such as dimethyl ether, etc.

However, this type of insecticidal aerosols, when put to practical use, have serious problems that corrosion occurs on the inner wall of the aerosol container made of tinplate during the storage, which in turn causes the leak of the propellant gas, and that the effect of the aerosols is lowered by the decomposition of the insecticidal compound contained in the aerosols.

The present inventors have extensively studied to develop a mono-layer liquid phase type water-based insecticidal aerosol not causing such the problems, and as a result, have found that a mono-layer liquid phase type water-based insecticidal aerosol which comprises (A) a base liquid for aerosol containing as an insecticidally active ingredient at least one pyrethroidal compound selected from the group consisting of:

3-phenoxybenzyl 2,2-dimethyl-3-(2,2-dichlorovinyl)cyclopropanecarboxylate (permethrin),
3-phenoxybenzyl chrysanthemate (phenothrin),
5-benzyl-3-furylmethyl chrysanthemate (resmethrin),
1-ethynyl-2-methyl-2-pentenyl chrysanthemate,
2-(4-ethoxyphenyl)-5-(4-fluoro-3-phenoxy)phenyl-2-methylpentane and
2-[1-methyl-2-(4-phenoxyphenoxy)ethoxy]pyridine (pyriproxyfen), an organic solvent selected from the group consisting of:

isopropyl alcohol,
n-propyl alcohol,
ethyl alcohol,
propylene glycol,
propylene glycol methyl ether,
dipropylene glycol methyl ether,
tripropylene glycol methyl ether and acetone, and a buffer solution, which base liquid has a pH of from 7.0 to 11.0, and (B) dimethyl ether as a propellant, can be suited to this object. The present inventors thus attained to the present invention.

The insecticidal aerosol of the present invention can be kept in a homogeneous liquid phase without causing separation in two layers even when it is stored for a long period of time at a relatively high temperature. In addition, there is no generation of rust on the wall of the aerosol container, and the insecticidally active ingredient remains stable.

Accordingly, the insecticidal aerosol of the present invention can be used as they are and requires no previous shaking at the time of application, and also they can exhibit an excellent effect as an insecticide.

Each of the pyrethroidal compounds belonging to the foregoing group used as the insecticidally active ingredient has steric and optical isomers. And these. isomers and their mixtures may be used in the present invention.

The insecticidally active ingredient is usually blended in the aerosol in an amount of 0.01 to 2% by weight, preferably 0.03 to 1% by weight based on the total weight of the aerosol.

Specific examples of the buffer solutions are
ammonium benzoate-NaOH buffer solution,
sodium benzoate-benzoic acid buffer solution,
ammonium benzoate-ammonia buffer solution,
ammonium benzoate-benzoic acid buffer solution,
$KH_2PO_4$-NaOH buffer solution,
NaOH-sodium bimaleate buffer solution,
tris.maleate*-NaOH buffer solution and
* mixture of tris(hydroxymethyl)aminomethane and maleic acid
$Na_2CO_3$-$NaHCO_3$ buffer solution.

The buffer solution is incorporated in the aerosol in an amount of 10 to 55% by weight, preferably from 20 to 50% by weight based on the total weight of the aerosol.

The amount of dimethyl ether, a propellant, used is usually from 10 to 80% by weight, preferably from 30 to 60% by weight based on the total weight of the aerosol.

The amount of the organic solvent used is usually from 10 to 70% by weight, preferably from 18 to 40% by weight.

In the insecticidal aerosols of the present invention, surface active agents, synergists, perfumes, fungicides, etc. may be used together if necessary.

As the synergists, conventional ones such as piperonyl butoxide, S-421, MGK-264, Synepirin, etc. may be used.

The insecticidal aerosols of the present invention may be prepared, for example, by the following method: Prescribed amounts of the insecticidally active ingredient, organic solvents and if necessary, surface active agents, synergists, perfumes, fungicides, etc. are mixed at room temperature or under heating and put in an aerosol container; a prescribed amount of the buffer solution having a prescribed pH value is added, and the base liquid for aerosol thus obtained is conditioned so as to have a pH in a range of from 7.0 to 11.0; and after mounting a valve portion on the aerosol container, dimethyl ether is charged into the container under pressure through the valve portion.

The present invention will be illustrated in more detail with reference to the following examples and comparative examples, but it is not limited to these examples.

In the following examples, parts mean a part by weight.

EXAMPLE 1

0.3 Part of phenothrin and 24.7 parts of isopropyl alcohol were well mixed under heating and introduced into an aerosol container made of tinplate. To the mixture were added 30.0 parts of an ammonium benzoate-ammonia buffer solution, which had been prepared by adding a 29% aqueous ammonia to a 1.0% w/w aqueous ammonium benzoate solution and then conditioning the pH of the solution to 11.3. Thus, a base liquid for aerosol having a pH of 11.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed It was found that the aerosol was not recognized to be separated, remaining homogeneous and transparent. The content of phenothrin in the aerosol was determined by gas chromatography under the following conditions and compared with the content which had been determined immediately after preparation of the aerosol. As a result, the percentage of the remainder of phenothrin was found to be 95.5%.

The generation of rust on the wall of the aerosol container was not observed.

Apparatus: FID

Column: 2% DEGS [Chromosorb W (AW, DMCS, 100–120 mesh)].

Glass column of 1.1 m×3 mmφ in size.

Column temperature: 210° C.

$N_2$ flow rate: 50 ml/min

Internal standard: Tetramethrin

EXAMPLE 2

0.3 Part of resmethrin and 24.7 parts of isopropyl alcohol were well mixed under heating and introduced into an aerosol container made of tinplate. To the resulting mixture were added 30.0 parts of an ammonium benzoate-NaOH buffer solution, which had been prepared by adding a 10% w/w aqueous NaOH solution to a 1.0% w/w aqueous ammonium benzoate solution and then conditioning the pH of the solution to 11.3. Thus, a base liquid for aerosol having a pH of 11.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed It was found that the aerosol was not recognized to be separated, remaining homogeneous and transparent. The content of resmethrin in the aerosol was determined by gas chromatography under the following conditions and compared with the content which had been determined immediately after preparation of the aerosol. As a result, the percentage of the remainder of resmethrin was found to be 93.8%.

The generation of rust on the wall of the aerosol container was not observed.

Apparatus, column, column temperature and $N_2$ flow rate: Same as in Example 1.

Internal standard: Phenothrin

EXAMPLE 3

0.3 Part of permethrin, 0.5 part of sorbitan monolaurate and 24.2 parts of isopropyl alcohol were well mixed under heating and introduced into an aerosol container made of tinplate. To the mixture were added 20.0 parts of an ammonium benzoate-ammonia buffer solution, which had been prepared by adding a 29% aqueous ammonia to a 1.0% w/w aqueous ammonium benzoate solution and then conditioning the pH of the solution to 11.3. Thus, a base liquid for aerosol having a pH of 11.0 was prepared. Thereafter, a valve portion was mounted on the aerosol container, and 55.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The content of permethrin in the aerosol was determined by gas chromatography in the same manner as in Example 1 and compared with the content which had been determined immediately after preparation of the aerosol. As a result, the percentage of the remainder of permethrin was found to be 91.9%.

The generation of rust on the wall of the aerosol container was not observed.

EXAMPLE 4

0.3 Part of (RS)-1-ethynyl-2-methyl-2-pentenyl (1R)-cis, trans-chrysanthemate (empenthrin) and 24.7 parts of pro-bylene glycol were well mixed under heating and introduced into an aerosol container made of tinplate. To the resulting mixture were added 30.0 parts of an ammonium benzoate-ammonia buffer solution, which had been prepared by adding a 29% aqueous ammonia to a 1.0% w/w aqueous ammonium benzoate solution and then conditioning the pH of the mixed solution to 10.5. Thus, a base liquid for aerosol having a pH of 10.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The content of empenthrin in the aerosol was determined by gas chromatography under the following conditions and compared with the content which had been determined immediately after preparation of the aerosol. As a result, the percentage of the remainder of empenthrin was found to be 98.7%.

The generation of rust on the wall of the aerosol container was not observed.

Apparatus: FID

Column: 5% SE-30 [Uniport HP (100–120 mesh)].

Glass column of 1.1 m×3 mmφ in size.

Column temperature: 150° C.

$N_2$ flow rate: 50 ml/min

Internal standard: Dimethyl phthalate

EXAMPLE 5

0.3 Part of pyriproxyfen and 24.7 parts of ethyl alcohol were well mixed under heating and introduced into an aerosol container made of tinplate. To the mixture were added 30.0 parts of an ammonium benzoate-ammonia buffer solution, which had been prepared by adding a 29% aqueous ammonia to a 1.0% w/w aqueous ammonium benzoate solution and then conditioning the pH of the mixed solution to 10.5. Thus, a base liquid for aerosol having a pH of 10.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The content of pyriproxyfen in the aerosol was determined by gas chromatography under the following conditions and compared with the content which had been determined immediately after preparation of the aerosol. As a result, the percentage of the remainder of pyriproxyfen was found to be 97.0%.

The generation of rust on the wall of the aerosol container was not observed.

Apparatus: FID

Column: 5% OV-101 [Uniport HP (100–120 mesh)]. Glass column of 1.1 m×3 mmφ in size.

Column temperature: 260° C.

$N_2$ flow rate: 50 ml/min

Internal standard: Triphenyl phosphate

EXAMPLE 6

0.3 Part of 2-(4-ethoxyphenyl)-5-(4-fluoro-3-phenoxy)phenyl-2-methylpentane and 24.7 parts of tripropylene glycol methyl ether were well mixed under heating and introduced into an aerosol container made of tinplate. To the mixture were added 30.0 parts of an ammonium benzoate-ammonia buffer solution, which had been prepared by adding a 29% aqueous ammonia to a 1.0% w/w aqueous ammonium benzoate solution and then conditioning the pH of the mixed solution to 10.5. Thus, a base liquid for aerosol having a pH of 10.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The content of 2-(4-ethoxyphenyl)-5-(4-fluoro-3-phenoxy)phenyl-2-methylpentane in the aerosol was determined by gas chromatography in the same manner as in Example 5 and compared with the content which had been determined immediately after preparation of the aerosol. As a result, the percentage of the remainder of 2-(4-ethoxyphenyl)-5-(4-fluoro-3-phenoxy)phenyl-2-methylpentane was found to be 92.1%.

The generation of rust on the wall of the aerosol container was not observed.

COMPARATIVE EXAMPLE 1

An aerosol was prepared in the same manner as in Example 3 except that an ammonium benzoate-ammonia buffer solution having a pH of 13.3 was used, and that the pH of the base liquid for aerosol was conditioned to 13.0.

The insecticidal aerosol thus obtained was stored at 45° C. for 3 months. Then the permethrin in the aerosol was determined by gas chromatography in the same manner as in Example 3 and compared with the content which had been determined immediately after preparation of the aerosol. As a result, the percentage of the remainder of permethrin was found to be 54.3%.

In addition, the generation of rust on the wall of the aerosol container was observed.

What is claimed is:

1. A mono-layer liquid phase type water-based insecticidal aerosol which comprises
   (A) a base liquid for aerosol containing as an insecticidally active ingredient at least one pyrethroidal compound selected from the group consisting of:
   3-phenoxybenzyl 2,2-dimethyl-3-(2,2-dichlorovinyl)-cyclopropanecarboxylate (permethrin),
   3-phenoxybenzyl chrysanthemate (phenothrin),
   5-benzyl-3-furylmethyl chrysanthemate (resmethrin),
   1-ethynyl-2-methyl-2-pentenyl chrysanthemate,
   2-(4-ethoxyphenyl)-5-(4-fluoro-3-phenoxy)phenyl-2-methylpentane and
   2-[1-methyl-2-(4-phenoxyphenoxy)ethoxy]pyridine (pyriproxyfen),
   an organic solvent selected from the group consisting of:
   isopropyl alcohol,
   n-propyl alcohol,
   ethyl alcohol,
   propylene glycol,
   propylene glycol methyl ether,
   dipropylene glycol methyl ether,
   tripropylene glycol methyl ether and acetone,
   and a buffer solution, which base liquid has a pH of from 7.0 to 11.0, and
   (B) dimethyl ether as a propellant.

2. An aerosol according to claim 1, wherein dimethyl ether as a propellant is blended in the aerosol in an amount of 10 to 80% by weight based on the total weight of the aerosol.

3. An aerosol according to claim 1, which comprises an organic solvent selected from the group consisting of isopropyl alcohol, n-propyl alcohol, ethyl alcohol, propylene glycol, propylene glycol methyl ether, dipropylene glycol methyl ether, tripropylene glycol methyl ether and acetone in an amount of from 10 to 70% by weight based on the total weight of the aerosol.

4. An aerosol according to claim 1, which comprises a buffer solution of from 10 to 55% by weight based on the total weight of the aerosol.

5. An aerosol according to claim 1, which comprises said pyrethroidal compound in an amount of from 0.01 to 2% by weight based on the total weight of the aerosol.

* * * * *